A61K 7/46

(12) United States Patent
Kuhn et al.

(10) Patent No.: US 6,914,109 B2
(45) Date of Patent: Jul. 5, 2005

(54) PROCESS FOR THE PREPARATION OF 15-PENTADECANOLIDE

(75) Inventors: Walter Kuhn, Holzminden (DE); Oskar Koch, Göttingen (DE); Hans-Ulrich Funk, Lauenförde (DE); Gerhard Senft, Holzminden (DE)

(73) Assignee: Symrise GmbH & Co. KG (DE)

( * ) Notice: Subject to any disclaimer, the term of this patent is extended or adjusted under 35 U.S.C. 154(b) by 343 days.

(21) Appl. No.: 10/100,343

(22) Filed: Mar. 18, 2002

(65) Prior Publication Data

US 2002/0137948 A1 Sep. 26, 2002

(30) Foreign Application Priority Data

Mar. 22, 2001 (DE) .......................... 101 13 963

(51) Int. Cl.$^7$ ............................................... A61K 7/46
(52) U.S. Cl. ..................... 526/171; 526/281; 526/283; 526/308; 512/11; 512/25; 512/26; 525/245; 549/267; 549/347; 549/396; 549/222; 549/266; 556/13; 556/22; 556/32; 556/136; 568/338; 568/361; 568/365; 568/643

(58) Field of Search ........................... 512/11, 25, 26; 526/171, 281, 283, 308; 525/245; 549/267, 347, 396, 222, 266; 556/13, 22, 32, 136; 568/338, 361, 365, 643

(56) References Cited

U.S. PATENT DOCUMENTS

| | | | | | |
|---|---|---|---|---|---|
| 3,890,353 A | * | 6/1975 | Becker | ..................... | 549/266 |
| 3,904,651 A | * | 9/1975 | Becker | ..................... | 549/396 |
| 5,214,163 A | * | 5/1993 | Fankhauser et al. | ........ | 549/396 |
| 5,266,559 A | * | 11/1993 | Fankhauser et al. | .......... | 512/11 |
| 5,319,104 A | * | 6/1994 | Hopp et al. | ................. | 549/222 |
| 5,936,100 A | * | 8/1999 | Furstner et al. | ............. | 549/266 |
| 6,008,185 A | * | 12/1999 | Bertram et al. | ............... | 512/12 |
| RE36,493 E | * | 1/2000 | Mimoun et al. | .............. | 512/11 |
| 6,590,048 B1 | * | 7/2003 | Furstner et al. | ............. | 526/171 |

* cited by examiner

*Primary Examiner*—Monique T. Cole
(74) *Attorney, Agent, or Firm*—Pendorf & Cutliff

(57) ABSTRACT

The invention relates to a process for the preparation of 15-pentadecanolide by hydrogenating 15-pentadecenolide and to its use.

11 Claims, No Drawings

PROCESS FOR THE PREPARATION OF 15-PENTADECANOLIDE

FIELD OF THE INVENTION

The invention relates to a process for the preparation of 15-pentadecanolide by hydrogenating 15-pentadecenolide and to its use.

BACKGROUND OF THE INVENTION

15-Pentadecanolide (oxacyclohexadecan-2-one) is a valuable musk odorant which occurs in angelica root oil (K. Bauer, A. Garbe, Common Fragrance and Flavor Materials, p. 104, VCH, Weinheim, 1985).

It is known to prepare 15-pentadecanolide by hydrogenating the double bond of 15-pentadecenolide.

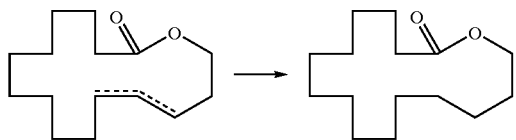

15-Pentadecenolide can be prepared according to Russian Chemical Bulletin, 47, 6, 1998, 1166 and is usually in the form of a mixture of 15-pentadecen-11-olide and 15-pentadecen-12-olide. This double bond isomer mixture is referred to in the present case as 15-pentadecen-11(12)-olide.

In JP 01090182 A2 (Chemical Abstract Number 1989 : 534017), the catalyst used is Raney nickel for hydrogenating 15-pentadecen-11(12)-olide in ethanolic solution.

Russian Chemical Bulletin, 47, 6, 1998, 1166 describes palladium catalysts for the hydrogenation. 15-Pentadecen-11(12)-olide is hydrogenated with palladium on activated carbon or palladium on aluminum oxide to give 15-pentadecanolide, optionally with the addition of a base such as sodium carbonate.

The processes for the preparation of 15-pentadecanolide from 15-pentadecen-11(12)-olide mentioned exhibit serious disadvantages in cases of industrial production. In addition to the high hydrogen pressures and any additions of base, the dilution with solvents and the high use amount of catalyst are particularly disadvantageous. In the case of Raney nickel, the pyrophoric, toxic and allergenic properties of the catalyst are particularly disadvantageous.

In general, the 15-pentadecanolide originating from these hydrogenations has following the thermal stress of a distillation, a scorched note in terms of odor, which often requires further purification in order to obtain a perfumistically acceptable quality.

There is also the need to find a process which produces 15-pentadecanolide in an economic manner, in a high yield and of a good perfumistic quality.

SUMMARY OF THE INVENTION

The invention relates to a process for the preparation of 15-pentadecanolide by hydrogenating 15-pentadecen-11(12)-olide in the presence of a catalyst comprising at least one metal of subgroup 8 in elemental form, which is optionally applied to a support, wherein the weight ratio of metal to 15-pentadecen-11(12)-olide is below 1:20,000.

The present invention further provides a process for the preparation of 15-pentadecanolide by hydrogenating 15-pentadecen-11(12)-olide in the presence of a catalyst comprising at least one metal from subgroup 8 in elemental form, which may be applied to a support, wherein the hydrogenation crude product has an acid number of at most 1.

DETAILED DESCRIPTION OF THE INVENTION

The acid number corresponds to the number of milligrams of potassium hydroxide which are consumed to neutralize the free organic acids of one gram of the hydrogenation crude product.

The hydrogenation crude product is understood as meaning the product originating directly from the hydrogenation, i.e. the crude 15-pentadecanolide present without further purification.

The 15-pentadecanolide prepared in this way already has perfumistic quality in the form of the hydrogenation crude product and requires no further purification. If desired, further purification can be carried out. The yield is virtually quantitative (yield of 15-pentadecanolide greater than 98.5%). The hydrogenation is preferably carried out without solvents. The process according to the present invention permits hydrogenation under mild conditions.

According to the present invention, catalysts are understood as meaning materials which have catalytic action in the hydrogenation in the process according to the present invention.

The catalysts according to the present invention comprise at least one metal of subgroup 8 in elemental metallic form.

These metals can be used, for example, in finely divided form, applied to supports or together with other metals (e.g. metals, alloys). The catalysts can comprise dopings with one or more desired metals.

Suitable catalysts can comprise, for example, ruthenium, rhodium, iridium, nickel, palladium or platinum. For the purposes of the process according to the present invention, advantageous catalysts comprise palladium, platinum, ruthenium or rhodium. A more preferred metal is palladium.

The metals according to the present invention can be applied to organic or inorganic support materials. The catalysts can comprise a support material or mixtures of support materials. Suitable support materials which may be mentioned are activated carbon, carbon, aluminum oxides, metal oxides, silica gels, zeolites, clays, clay granules, amorphous aluminum silicates or other inorganic supports. A preferred support material is activated carbon.

A more preferred catalyst is palladium on activated carbon.

In the process according to the present invention, catalyst amounts are used in which the weight ratio of the amount of metal to 15-pentadecen-11(12)-olide is below 1:20,000, preferably in the range 1:50 000 to 1:10,000,000, more preferably in the range 1:100,000 to 1:5,000,000 and most preferably in the range 1:250,000 to 1:1,000,000.

The amount of metal refers here to the absolute content of the metal of subgroup 8 or the total content of metals of subgroup 8, i.e. without support material and without diluents or water, which may be present.

If catalysts comprising support materials are used, the proportion of metal on the support material can generally be 0.5 to 50% by weight, preferably 1 to 20% by weight, and more preferably 3 to 10% by weight, based on the dry catalyst.

For the process according to the present invention, the catalyst can be used in the dry or moist state (residual moisture of water).

The process according to the present invention can be carried out in the presence of solvents, but preference is given to a solvent-free hydrogenation.

The hydrogenation can be carried out at temperatures of from 0 to 150° C. Suitable temperatures are those in the range from 20 to 100° C., preferably in the range from 30 to 90° C., more preferably 45 to 80° C. Most preferably, the temperature range is from 60 to 75° C.

According to the present invention, the hydrogenations are carried out with elemental hydrogen.

The hydrogen pressure is suitably 1 to 100 bar, preferably 1 to 30 bar, more preferably 5 to 20 bar.

The reaction time is preferably 1 to 100 hours, more preferably 10 to 50 hours.

The acid number of the hydrogenation crude product (crude 15-pentadecanolide) has acid numbers of at most 1 mg of potassium hydroxide/g of product.

The 15-pentadecanolide prepared by the process according to the present invention can be used without further purification steps, and, in particular, it has a good perfumistic quality.

The 15-pentadecanolide prepared by the process according to the invention can be used, in particular, as odorant in perfume compositions, perfume oils or scent compositions.

A further field of use is hygiene and care products, in particular in the domestic and toiletries sector.

The perfume oils comprising the 15-pentadecanolide prepared by the process according to the present invention can be used in concentrated form, in solutions or in another modified form for the preparation of, for example, perfume extracts, eaux de parfum, eaux de toilette, aftershaves, eaux de cologne, pre-shave products, splash colognes and perfumed freshening wipes, and the perfuming of acidic, alkaline and neutral cleaners, such as, for example, floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and bodycare compositions, such as, for example, solid and liquid soaps, shower gels, shampoos, shaving soaps, shaving foams, bath oils, cosmetic emulsions of the oil-in-water type, of the water-in-oil type and of the water-in-oil-in-water type, such as, for example, skin creams and lotions, face creams and lotions, sunscreen creams and lotions, aftersun creams and lotions, handcreams and lotions, foot creams and lotions, depilatory creams and lotions, aftershave creams and lotions, tanning creams and lotions, haircare products, such as, for example, hairsprays, hair gels, hair lotions, hair rinses, permanent and semi-permanent hair colorants, hair-shaping compositions, such as cold waves and hair-smoothing compositions, hair tonics, hair creams and lotions, deodorants and antiperspirants, such as, for example, underarm sprays, roll-ons, deodorant sticks, deodorant creams or products of decorative cosmetics.

The examples below illustrate the invention.

EXAMPLE 1

In Example 1, the ratio of Pd:15-pentadecen-11(12)-olide is 1:281,667

2,535 kg of 15-pentadecen-11(12)-olide (GC content of 15-pentadecen-11(12)-olide isomers: 93.2%; GC content of 15-pentadecanolide 2.9%) and 300 g of palladium on activated carbon (Pd content: 5% by weight) with a water content of 40% were introduced into a 4 m$^3$ stirred autoclave with gas-dispersion stirrer. Hydrogenation was carried out for 12 hours at 68–70° C. and a hydrogen pressure of 20 bar. Filtration of the hydrogenation crude product gave 2,548 kg of 15-pentadecanolide in 95.4% purity. The yield was >99%. The melting point was 31° C. The acid number of the hydrogenation crude product was 0.6. The resulting product has a good perfumistic quality.

EXAMPLE 2

In Example 2, the ratio of Pd:15-pentadecen-11(12)-olide is 1:845,000

2,535 kg of 15-pentadecen-11(12)-olide (GC content: see Example 1) and 100 g of palladium on activated carbon (Pd content: 5% by weight) with a water content of 40% were introduced into a 4 m$^3$ stirred autoclave with gas-dispersion stirrer. Hydrogenation was carried out for 44 hours at 68–69° C. and a hydrogen pressure of 20 bar. Filtration of the hydrogenation crude product gave 15-pentadecanolide in 95.8% purity. The yield was >99%. The melting point was 31° C. The acid number of the hydrogenation crude product was 0.7. The product obtained in this way has a good perfumistic quality.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of 15-pentadecanolide by hydrogenating 15-pentadecen-11(12)-olide in the presence of a catalyst comprising at least one metal of subgroup 8 in elemental form, which is optionally applied to a support, wherein the weight ratio of metal to 15-pentadecen-11(12)-olide is below 1:20,000.

2. A process according to claim 1, wherein the metal of subgroup 8 used is selected from the group consisting of palladium, platinum, ruthenium or rhodium.

3. A process according to claim 2, wherein the metal used is palladium.

4. A process according to claim 1, wherein the catalyst comprises at least one inorganic support material.

5. A process according to claim 1, wherein the catalyst used is palladium on activated carbon.

6. A process according to claim 1, wherein the weight ratio of amount of metal to 15-pentadecen-11(12)-olide is in the range 1:50,000 to 1:10,000,000.

7. A process according to claim 1, wherein hydrogenation is carried out at temperatures in the range from 20 to 100° C.

8. A process according to claim 1, wherein hydrogenation is carried out without a solvent.

9. A process according to claim 1, wherein hydrogen pressure is 1 to 100 bar.

10. A process for the preparation of 15-pentadecanolide by hydrogenating 15-pentadecen-11(12)-olide in the presence of a catalyst comprising at least one metal from subgroup 8 in elemental form, which may be applied to a support, wherein the hydrogenation crude product has an acid number of at most 1.

11. A process according to claim 10, wherein the hydrogenation crude product is not purified.

* * * * *